(12) United States Patent
Kim et al.

(10) Patent No.: US 12,193,802 B2
(45) Date of Patent: Jan. 14, 2025

(54) BLOOD FLOW MEASUREMENT DEVICE AND BLOOD FLOW MEASUREMENT METHOD

(71) Applicant: KOH YOUNG TECHNOLOGY INC., Seoul (KR)

(72) Inventors: Hong Ki Kim, Yongin-si (KR); Young Joo Hong, Gwangmyeong-si (KR); Deok Hwa Hong, Gwangmyeong-si (KR); Guk Bin Lim, Changwon-si (KR); Seung Tae Kim, Seoul (KR); Min Kyu Kim, Gwangmyeong-si (KR); Eun Ha Jo, Gwangmyeong-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 519 days.

(21) Appl. No.: 17/430,225

(22) PCT Filed: Feb. 11, 2020

(86) PCT No.: PCT/KR2020/001884
§ 371 (c)(1),
(2) Date: Aug. 11, 2021

(87) PCT Pub. No.: WO2020/166929
PCT Pub. Date: Aug. 20, 2020

(65) Prior Publication Data
US 2022/0160246 A1    May 26, 2022

Related U.S. Application Data

(60) Provisional application No. 62/804,061, filed on Feb. 11, 2019, provisional application No. 62/840,011, filed on Apr. 29, 2019.

(51) Int. Cl.
*A61B 5/026* (2006.01)
*A61B 5/00* (2006.01)

(52) U.S. Cl.
CPC .......... *A61B 5/0261* (2013.01); *A61B 5/7278* (2013.01); *A61B 5/742* (2013.01); *A61B 2562/0233* (2013.01)

(58) Field of Classification Search
CPC .................................................... A61B 5/0261
See application file for complete search history.

(56) References Cited

U.S. PATENT DOCUMENTS

| 4,746,211 A | 5/1988 | Ruth et al. |
| 5,620,000 A | 4/1997 | Zinser et al. |

(Continued)

FOREIGN PATENT DOCUMENTS

| DE | 20 2016 104 220 | 9/2016 |
| JP | 64-37931 | 2/1989 |

(Continued)

OTHER PUBLICATIONS

Office Action from Intellectual Property of India corresponding to India Application No. 202117039346, dated Mar. 2, 2022.

(Continued)

*Primary Examiner* — Colin T. Sakamoto
(74) *Attorney, Agent, or Firm* — KILE PARK REED & HOUTTEMAN PLLC

(57) ABSTRACT

A blood flow measurement device according to various embodiments may be configured to irradiate light to a first position of a subject and a second position of the subject located in a first direction with respect to the first position, acquire intensities of the reflected light at the first position and the second position, determine a first value which is a difference between the intensities of the reflected light at the first position and the second position, irradiate light to a third position of the subject located in a second direction with respect to the second position, acquire an intensity of the reflected light at the third position, determine a second value (Continued)

which is a difference between the intensities of the reflected light at the second position and the third position, and determine a blood flow direction based on the first value and the second value.

10 Claims, 12 Drawing Sheets

(56) References Cited

U.S. PATENT DOCUMENTS

| | | |
|---|---|---|
| 2002/0104957 A1 | 8/2002 | Liess et al. |
| 2003/0006367 A1 | 1/2003 | Liess et al. |
| 2003/0016365 A1 | 1/2003 | Liess et al. |
| 2008/0208022 A1 | 8/2008 | Kruger et al. |
| 2008/0234590 A1 | 9/2008 | Akkermans et al. |
| 2009/0209871 A1 | 8/2009 | Ueki et al. |
| 2010/0280398 A1 | 11/2010 | Hachiga et al. |
| 2013/0116575 A1 | 5/2013 | Mickle et al. |
| 2017/0164844 A1 | 6/2017 | Yamada |
| 2017/0251930 A1 | 9/2017 | Machida et al. |
| 2017/0347880 A1 | 12/2017 | Akiba |
| 2018/0303429 A1 | 10/2018 | Machida et al. |
| 2019/0029636 A1 | 1/2019 | Lee et al. |
| 2019/0167118 A1 | 6/2019 | Vilenskii et al. |
| 2019/0380598 A1 | 12/2019 | Higuchi |
| 2020/0029809 A1 | 1/2020 | Akiba |

FOREIGN PATENT DOCUMENTS

| | | |
|---|---|---|
| JP | H07-31596 | 2/1995 |
| JP | H07-163534 | 6/1995 |
| JP | 2004-513352 | 4/2004 |
| JP | 3576212 | 10/2004 |
| JP | 2007-534421 | 11/2007 |
| JP | 2008-142252 | 6/2008 |
| JP | 2008-278993 | 11/2008 |
| JP | 2009-189651 | 8/2009 |
| JP | 2010-110371 | 5/2010 |
| JP | 2017-153875 | 9/2017 |
| JP | 2018-7894 | 1/2018 |
| JP | 2018-183375 | 11/2018 |
| KR | 10-0813428 | 3/2008 |
| KR | 10-1123179 | 3/2012 |
| KR | 10-2017-0091956 | 8/2017 |
| KR | 10-2018-0018318 | 2/2018 |
| KR | 10-1879634 | 7/2018 |
| WO | 2009/081883 | 7/2009 |
| WO | 2016/098473 | 6/2016 |

OTHER PUBLICATIONS

Korean Office Action with English translation for Korean Application No. 10-2023-7036523, dated Nov. 6, 2023.
Extended European Search Report for European Application No. 23194779.7 dated Nov. 15, 2023.
Chinese Office Action with English translation for Chinese Application No. 202080013664.5, dated Dec. 28, 2023.
Korean Office Action with English translation for Korean Patent Application No. 10-2021-7025492, dated Jan. 31, 2023.
Wearable laser blood flowmeter. YouTube. (Aug. 16, 2015a). https://youtu.be/5Pe1l9gkVJM.
Japanese Office Action with English translation for Japanese Patent Application No. 2023-070196, dated Jan. 30, 2024.
Indian Office Action with English translation for Indian Patent Application No. 202117039346, dated Jan. 31, 2024.
Japanese Office Action, with English translation, for Japanese Patent Application or Patent No. 2021-547148 dated Aug. 1, 2022.
Extended European Search Report for European Application No. or Patent No. 20756471.7 dated Sep. 30, 2022.
International Search Report with English translation for International Application No. PCT/KR2020/001884, dated May 20, 2020.
Written Opinion with English translation for International Application No. PCT/KR2020/001884, dated May 20, 2020.
Korean Office Action with English translation for Korean Patent Application No. 10-2023-7036523, dated Jun. 24, 2024.

BLOOD FLOW MEASUREMENT DEVICE AND BLOOD FLOW MEASUREMENT METHOD

CROSS-REFERENCE TO RELATED APPLICATION(S)

This application is a national entry of International Application No. PCT/KR2020/001884, filed on Feb. 11, 2020, which claims priority to and benefits of U.S. Provisional Patent Application No. 62/804,061, filed on Feb. 11, 2019 and U.S. Provisional Patent Application No. 62/840,011, filed on Apr. 29, 2019, the entire contents of which are incorporated herein by reference.

TECHNICAL FIELD

Various embodiments disclosed herein relate to a blood flow measurement device and a blood flow measurement method using the same.

BACKGROUND

A method of measuring a blood flow using ultrasound may be a method of irradiating ultrasound to a surface of a subject, receiving reflected ultrasound, and non-invasively obtaining information about the blood flow.

In the case of a method of measuring a blood flow through the use of a light source (e.g., a laser), it may be a method of administering a contrast agent (e.g., indocyanine green (ICG)), which causes a fluorescence reaction, to a subject and acquiring a fluorescence image of blood vessels of the subject to obtain information on a blood flow.

In the case of a method of measuring a blood flow by using ultrasound, a probe that outputs ultrasound should be brought into contact with a surface of a subject. In this case, accurate information about the blood flow can be measured only when the probe is brought into contact with the surface of the subject at a specific angle.

In the case of a method of measuring a blood flow by using a light source, the presence or absence of a blood flow may be visually determined by using an image obtained through a fluorescence reaction. The method of measuring the blood flow through the fluorescence image is a qualitative method in which in order to confirm the direction of a blood flow in a specific blood vessel, it may be necessary to visually check the direction of the fluorescence reaction at a specified time (e.g., at the time when a contrast agent is administered and diffused into a specific blood vessel).

In the case of the method of measuring the blood flow by using the light source, the contrast agent needs to be administered to the blood vessel of the subject. Therefore, side effects may occur due to the contrast agent administration. The number of blood flow measurements may be limited in order to minimize the side effects of the contrast agent.

SUMMARY

A blood flow measurement device according to various embodiments of the present disclosure may include: a light output device configured to output light of a preset wavelength band; a light receiving sensor configured to receive the light outputted from the light output device and reflected by a subject; and a processor. The processor may be configured to: control the light output device to irradiate light to a first position of the subject and a second position of the subject located in a first direction with respect to the first position; acquire intensities of the reflected light at the first position and the second position from the light receiving sensor that receives the reflected light reflected at the first position and the second position; determine a first value which is a difference between the intensities of the reflected light at the first position and the second position; control the light output device to irradiate light to a third position of the subject located in a second direction opposite to the first direction with respect to the second position; acquire an intensity of the reflected light at the third position from the light receiving sensor that receives the reflected light reflected at the third position; determine a second value which is a difference between the intensities of the reflected light at the second position and the third position; and determine a blood flow direction in the subject based on the first value and the second value.

A blood flow measurement device according to various embodiments of the present disclosure may include: a light output device configured to output light of a preset wavelength band; a light receiving sensor configured to receive the light outputted from the light output device and reflected by a subject; and a processor. The processor may be configured to: control the light output device to irradiate light to a first position of the subject twice; acquire intensities of the reflected light at the first position twice from the light receiving sensor that receives the reflected light reflected at the first position twice; determine a difference between the intensities of the reflected light acquired twice to be a first value; and calculate a blood flow velocity in the subject based on the first value and pre-stored conversion information.

A blood flow measurement method according to various embodiments of the present disclosure using a blood flow measurement device, which includes a light output device configured to output light of a preset wavelength band, a light receiving sensor configured to receive the light outputted from the light output device and reflected by a subject, and a processor, may include: irradiating, by the light output device, light to a first position of the subject and a second position of the subject located in a first direction with respect to the first position; acquiring, by the processor, intensities of the reflected light at the first position and the second position from the light receiving sensor that receives the reflected light reflected at the first position and the second position; determining, by the processor, a first value which is a difference between the intensities of the reflected light at the first position and the second position; irradiating, by the light output device, light to a third position of the subject located in a second direction opposite to the first direction with respect to the second position; acquiring, by the processor, an intensity of the reflected light at the third position from the light receiving sensor that receives the reflected light reflected at the third position; determining, by the processor, a second value which is a difference between the intensities of the reflected light at the second position and the third position; and determining, by the processor, a blood flow direction in the subject based on the first value and the second value.

A blood flow measurement method according to various embodiments of the present disclosure using a blood flow measurement device, which includes a light output device configured to output light of a preset wavelength band, a light receiving sensor configured to receive the light outputted from the light output device and reflected by a subject, and a processor, may include: irradiating, by the light output device, light to a first position of the subject twice; acquiring, by the processor, intensities of the reflected light at the first position twice from the light receiving sensor that receives the reflected light reflected at the first position twice; determining, by the processor, a difference between the intensities of the reflected light acquired twice to be a first value; and calculating, by the processor, a blood flow velocity in the subject based on the first value and pre-stored conversion information.

The blood flow measurement device according to various embodiments of the present disclosure measures a blood flow through the use of a light source. Therefore, it is possible to acquire information on a blood flow without making direct contact with a surface of a subject.

The blood flow measurement device according to various embodiments of the present disclosure may acquire information on a blood flow by measuring the intensity of the reflected light emitted from a light source and reflected by a subject.

The blood flow measurement device according to various embodiments of the present disclosure uses a measurement value obtained by measuring the intensity of the reflected light without using a contrast agent. Therefore, it is possible to prevent the occurrence of side effects due to the use of a contrast agent, and to avoid limitations in the number of measurements and the measurement time.

DETAILED DESCRIPTION

Figure 1:
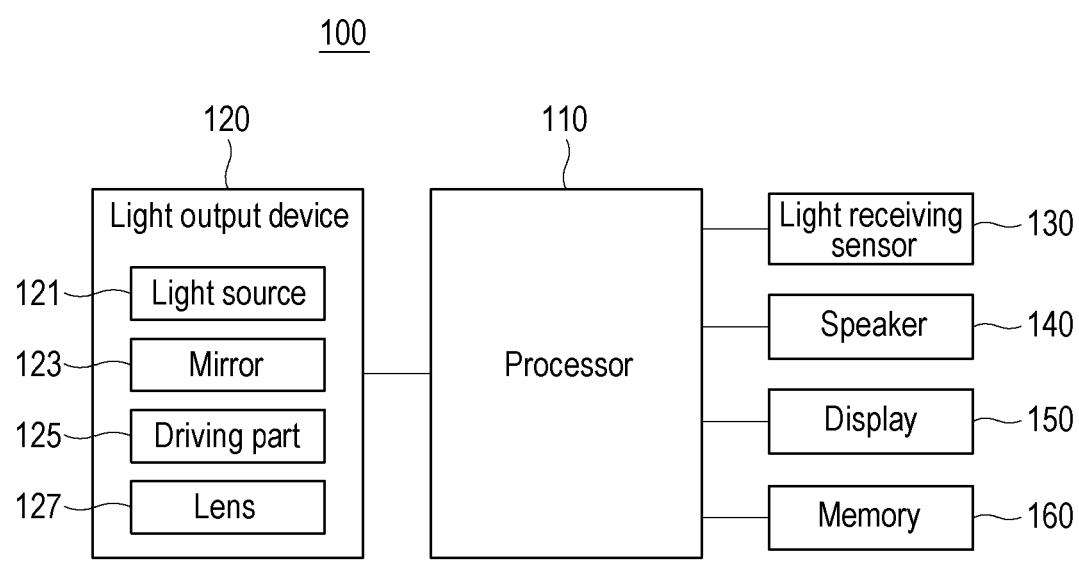
FIG. 1 illustrates a block diagram of a blood flow measurement device according to various embodiments of the present disclosure.

The various embodiments described herein are exemplified for the purpose of clearly describing the technical idea of the present disclosure, and are not intended to limit the technical idea of the present disclosure to specific embodiments. The technical idea of the present disclosure includes various modifications, equivalents, alternatives of each of the embodiments described in this document, and embodiments selectively combined from all or part of the respective embodiments. In addition, the scope of the technical idea of the present disclosure is not limited to various embodiments or detailed descriptions thereof presented below.

The terms used herein, including technical or scientific terms, may have meanings that are generally understood by a person having ordinary knowledge in the art to which the present disclosure pertains, unless otherwise specified.

As used herein, the expressions such as "include," "may include," "provided with," "may be provided with," "have," and "may have" mean the presence of subject features (e.g., functions, operations, components, etc.) and do not exclude the presence of other additional features. That is, such expressions should be understood as open-ended terms that imply the possibility of including other embodiments.

A singular expression can include meanings of plurality, unless otherwise mentioned, and the same is applied to a singular expression stated in the claims.

In connection with the description of the drawings, like reference numerals may be used for similar or related components. The singular form of a noun corresponding to an item may include one or more items, unless the relevant context clearly dictates otherwise. As used herein, each of the phrases such as "A or B," "at least one of A and B," "at least one of A or B," "A, B or C," "at least one of A, B and C," "at least one of A, B or C," and the like may include any one of items listed together in the corresponding one of the phrases, or all possible combinations thereof.

The terms "first," "second," and the like may be used to merely distinguish the corresponding components from one another, and are not intended to limit the corresponding components in other aspects (e.g., in terms of the importance or order).

The term "part" used herein may be a conception that comprehensively refers to software, or hardware components such as a field-programmable gate array (FPGA), an application specific integrated circuit (ASIC) and the like, and hardware components such as an optical element and the like. However, the term "part" is not limited to software and hardware. The term "part" may be configured to be stored in an addressable storage medium or may be configured to execute one or more processors. In one embodiment, the term "part" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables.

The expression "based on" used herein is used to describe one or more factors that influence a decision, an action of judgment or an operation described in a phrase or sentence including the relevant expression, and this expression does not exclude an additional factor influencing the decision, the action of judgment or the operation.

As used herein, the expression that a certain component (e.g., a first component) is "connected" to another component (e.g., a second component) may mean that the certain component is not only connected or coupled to another component directly, but also connected or coupled via a new other component (e.g., a third component).

As used herein, the expression "configured to" may have a meaning such as "set to," "having the ability to," "modified to," "made to," "capable of," or the like depending on the context. The expression is not limited to the meaning of "specially designed for hardware." For example, a processor configured to perform a specific operation may mean a generic-purpose processor capable of performing a specific operation by executing software.

Hereinafter, various embodiments of the present disclosure will be described with reference to the accompanying drawings. In the accompanying drawings and the descriptions of the drawings, the same reference numerals may be assigned to the same or substantially equivalent elements. Furthermore, in the following description of various embodiments, redundant descriptions of the same or corresponding elements may be omitted. However, this does not mean that the elements are not included in the embodiments.

FIG. 1 illustrates a block diagram of a blood flow measurement device according to various embodiments of the present disclosure.

Referring to FIG. 1, the blood flow measurement device 100 according to various embodiments may include a processor 110, a light output device 120, a light receiving sensor 130, a speaker 140, a display 150, and a memory 160. Even if some of the components shown in FIG. 1 are omitted or substituted, there will be no obstacle to implementing various embodiments disclosed herein.

According to various embodiments, the processor 110 may be a component capable of performing an operation or data processing related to control and/or communication of each component (e.g., the light output device 120) of the blood flow measurement device 100. The processor 110 may, for example, be operatively connected to components of the blood flow measurement device 100. The processor 110 may load commands or data received from other components of the blood flow measurement device 100 into the memory 160, may process the commands or data stored in the memory 160, and may store the resultant data.

The light output device 120 according to various embodiments may output light of a preset wavelength band and may irradiate a subject with the light. The light output device 120 may, for example, irradiate light to a specific position of a subject for which a blood flow is to be measured. The light output device 120 may move, for example, a region of the subject to which the light is irradiated, in a specific direction. For example, the light output device 120 may irradiate light to a first position of the subject and may irradiate light to a second position after a preset time has elapsed.

The light output device 120 according to various embodiments may include a light source 121, a mirror 123, a driving part 125, or a lens 127.

According to various embodiments, the light source 121 may output light of a preset wavelength band. The preset wavelength band may be, for example, a wavelength of an infrared band. The preset wavelength band is not limited to the wavelength of the infrared band, and may include a wavelength band visible to the human eye (e.g., a visible light band). The light source 121 may be, for example, a laser.

The mirror 123 according to various embodiments may change the path of the light so that the light outputted from the light source 121 can be irradiated to a target region on the subject. For example, the mirror 123 may rotate about an arbitrary axis.

The driving part 125 according to various embodiments may adjust the angle of the mirror 123 under the control of the processor 110. For example, the driving part 125 may rotate the mirror 123 in a specific direction in order to move a light irradiation position on the subject.

The lens 127 according to various embodiments may be a lens 127 that collimates incident light to pass through the lens 127 and travel in parallel. The lens 127 may be, for example, an f-theta lens 127 that corrects a focal point formed in an arc shape so as to be formed on one plane. The f-theta lens 127 may be, for example, a lens 127 that refracts and diffracts the irradiated light to correct a light path and a cross-sectional area of the light.

The light receiving sensor 130 according to various embodiments may receive the light outputted from the light output device 120 and reflected by the subject, and may generate an electrical signal indicating the intensity of the received light. This electrical signal may be transmitted to the processor 110.

The speaker 140 according to various embodiments may output various audio sounds under the control of the processor 110. The display 150 according to various embodiments may display various screens under the control of the processor 110.

The memory 160 according to various embodiments may store instructions for the operation of the processor 110.

Although the light receiving sensor 130 is shown as a separate configuration from the light output device 120 in FIG. 1, this is merely an example. In another embodiment, the light receiving sensor 130 may be included in the light output device 120. In addition, at least one of the mirror 123, the driver 125, and the lens 127 of the light output device 120 may be configured separately from the light output device 120.

Figure 2:
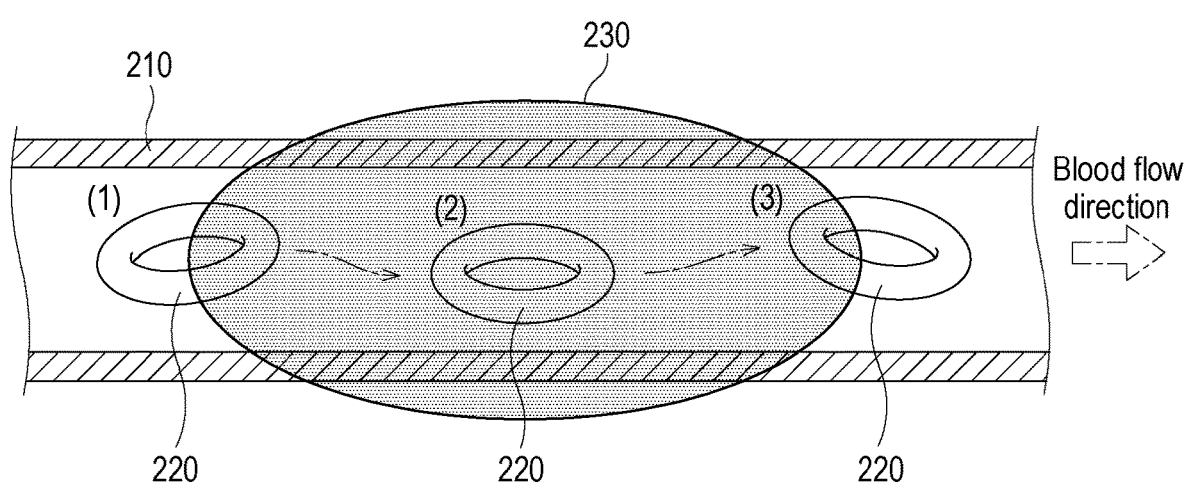
FIG. 2 illustrates a diagram of a blood flow measurement method according to various embodiments of the present disclosure.

FIG. 2 illustrates a diagram of a blood flow measurement method according to various embodiments of the present disclosure. For example, FIG. 2 may be a diagram illustrating a state in which light is irradiated to a blood vessel included in a target region of a subject.

Referring to FIG. 2, the processor 110 according to various embodiments may control the light output device 120 to irradiate light to a specific position within a target region of a subject. The target region of the subject may be, for example, a region of a predetermined size (e.g., 50 mm*50 mm) including a blood vessel 210 for which a blood flow is to be measured. The processor 110 may set the target region based on, for example, a user input.

According to various embodiments, the light of a preset wavelength band irradiated to a specific position of the subject may be reflected by reacting with a specific substance included in blood. According to various embodiments, the processor 110 may obtain the intensity of the reflected light at the specific position from the light receiving sensor 130 that receives the light reflected at the specific position. The processor 110 may, for example, irradiate light having a preset wavelength band to the specific position on the subject through the light output device 120. When the light outputted from the light output device 120 is reflected by the subject and received by the light receiving sensor 130, the light receiving sensor 130 may generate a signal indicating the intensity of the received light. The processor 110 may receive the signal from the light receiving sensor 130 and may determine the intensity of the reflected light from the specific position. For example, when laser light of an infrared wavelength band is irradiated, the irradiated light may be reflected by reacting with red blood cells 220 in the blood. The light receiving sensor 130 may receive the light reflected by the red blood cells 220 and may generate an electrical signal indicating the intensity of the received light. The processor 110 may receive the signal from the light receiving sensor 130 and may determine the intensity of the reflected light.

According to various embodiments, the measured intensity of reflected light may vary depending on the area occupied by the specific substance reacting with the light in the cross-sectional area 230 of the irradiated light. For example, as the area occupied by the red blood cells 220 in the cross-sectional area 230 of the irradiated light of an infrared band increases, the intensity of the measured reflected light may increase. For example, as the area occupied by the red blood cells 220 in the cross-sectional area 230 of the irradiated light of an infrared band decreases, the intensity of the reflected light may decrease.

As shown in FIG. 2, the specific substance (e.g., red blood cells 220) included in the blood vessel 210 of the subject may move from position (1) through position (2) to position (3) depending on the blood flow direction. When the red blood cells 220 are located at the position (1), the area of the red blood cells 220 included in the cross-sectional area 230 of the irradiated light is relatively small. Therefore, the intensity of the reflected light may be measured to be relatively small. When the red blood cells 220 are located at the position (2), the area of the red blood cells 220 included in the cross-sectional area 230 of the irradiated light is relatively large. Therefore, the intensity of the reflected light may be measured to be relatively large.

According to various embodiments, the processor 110 may calculate a blood flow velocity by measuring a change amount of the intensity of the reflected light at a specific position of the subject. For example, the processor 110 may irradiate light to a specific position (or a predetermined position) of the subject by using the light output device 120. The light receiving sensor 130 may measure the intensities of the reflected light from the specific position twice at a preset time interval. For example, the light receiving sensor 130 may receive reflected light from the specific position and generate an electrical signal indicating the intensity of the received light. The processor 110 may receive the signal from the light receiving sensor 130 and may determine the intensity of the reflected light. The processor 110 may calculate a difference between the measured values measured twice. The processor 110 may calculate a blood flow velocity based on the calculated difference value and pre-stored conversion information.

For example, when red blood cells are present at the position (1), it may be assumed that the intensity of reflected light measured by the processor 110 through the light receiving sensor 130 is 5. When the red blood cells move to the position (2) after the lapse of a preset time, for example, the intensity of the reflected light measured by the processor 110 through the light receiving sensor 130 may be 5.7. The processor 110 may calculate the difference between the intensities of the reflected light measured twice as 0.7.

For example, when red blood cells are present at the position (2), it may be assumed that the intensity of reflected light measured by the processor 110 through the light receiving sensor 130 is 5.7. When the red blood cells move to the position (3) after the lapse of a preset time, for example, the intensity of the reflected light measured by the processor 110 through the light receiving sensor 130 may be 5. The processor 110 may calculate the difference between the intensities of the reflected light measured twice as 0.7.

According to various embodiments, the blood flow measurement device 100 may output a sound corresponding to the measured blood flow velocity. The processor 110 may obtain a Doppler frequency corresponding to the calculated blood flow velocity based on the pre-stored conversion information. According to various embodiments, the processor 110 may output a sound corresponding to the acquired Doppler frequency through the speaker 140. The acquired Doppler frequency may be, for example, a frequency in the audible range. According to various embodiments, the processor 110 may display the calculated blood flow velocity and the acquired Doppler frequency through the display 150.

The pre-stored conversion information may include, for example, information on the correlation among the change amount of the intensity of the reflected light, the blood flow velocity, and the Doppler frequency thus acquired. The pre-stored conversion information may be, for example, an experimentally obtained table. The pre-stored conversion information may be stored in various forms including, for example, tables and functions.

Table 1 below is an example of a table obtained experimentally.

TABLE 1

| Doppler frequency (Hz) | Change amount of measured light intensity | Blood flow velocity (cm/s) |
| --- | --- | --- |
| 400 | 0.05 | 20 |
| 2,000 | 0.24 | 100 |
| 3,000 | 0.36 | 150 |
| 5,800 | 0.7 | 290 |

The change amount of the measured light intensity in Table 1 may be a digital value indicating the light intensity. The values listed in Table 1 are exemplary. The blood flow measurement device 100 may store experimental data measured for each blood vessel in the memory 160 in the form of a table.

For example, when the change amount of the intensity of reflected light measured at a preset time interval is 0.7, the processor 110 may determine the blood flow velocity of the blood vessel of the subject to be 290 cm/s. In this case, the processor 110 may determine the Doppler frequency corresponding to the blood flow velocity of 290 cm/s to be 5,800 Hz, based on the pre-stored conversion information. The processor 110 may output a sound corresponding to the frequency of 5,800 Hz through the speaker.

Figure 3:
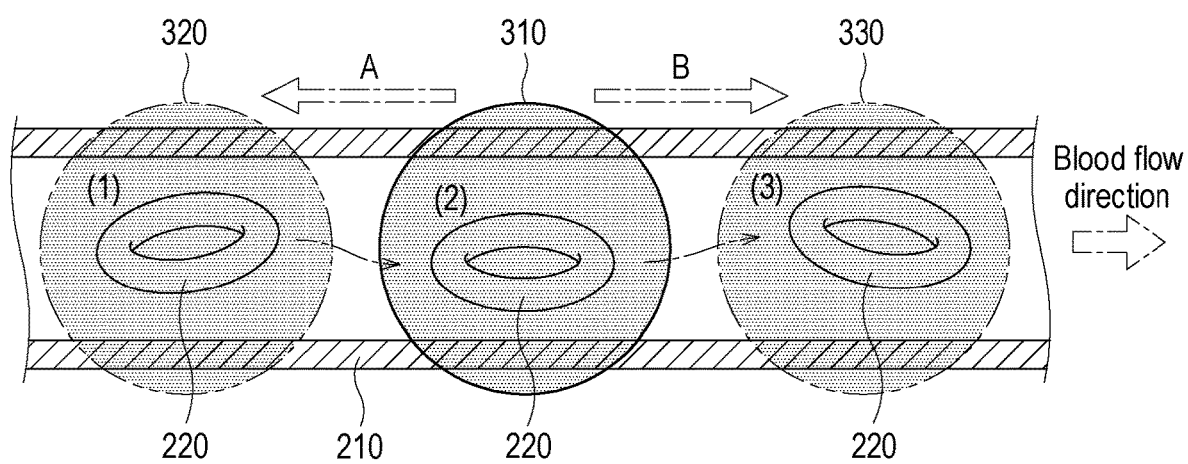
FIG. 3 illustrates a diagram of a blood flow measurement method according to various embodiments of the present disclosure.

FIG. 3 illustrates a diagram of a blood flow measurement method according to various embodiments of the present disclosure.

Referring to FIG. 3, according to various embodiments, the light output device 120 may change a position to which light is irradiated under the control of the processor 110. For example, the light output device 120 may move a light irradiated position in a specific direction. The light output device 120 may move, for example, a light irradiated position in an A direction from a first position 310 to a second position 320. For example, the light output device 120 may move a light irradiated position in a B direction from the first position 310 to a third position 330.

According to various embodiments, in response to the movement of the light irradiated position in the specific direction, the change amount of the intensity of the reflected light according to the movement may be determined. For example, when the light irradiated position is moved from the first position 310 to the second position 320, the processor 110 may control the light output device 120 so as to irradiate light to the first position 310 and the second position 320. The light receiving sensor 130 may receive the light reflected from the first position 310 and the second position 320, and may generate electrical signals indicating the intensities of the received light. The processor 110 may receive the electrical signals from the light receiving sensor 130 to determine the intensities of reflected light at the first position and the second position. The processor 110 may determine a difference between the intensities of the reflected light at the first position 310 and the second position 320 as a change amount of the reflected light intensity.

According to various embodiments, the processor 110 may acquire the intensities of the reflected light twice at a preset time interval from the light receiving sensor 130. For example, the processor 110 may acquire the intensities of reflected light from the light receiving sensor 130 twice at an interval of a preset time (e.g., 10 μs), and may calculate a difference between the values obtained twice. For example, when the light irradiated position is moved from the first position 310 to the second position 320, the processor 110 may control the light output device 120 so as to irradiate light to the first position 310 and irradiate light to the second position 320 after a preset time has elapsed from irradiation of light to the first position 310.

According to various embodiments, the blood flow measurement device 100 may measure the change amount of intensity of the reflected light for a preset time while moving the light irradiated position in two different directions. For example, in response to the movement of the light irradiated position in a first direction, the processor 110 may determine a first value which is the change amount of the intensity of the reflected light for a preset time. For example, in response to the movement of the light irradiated position in a second direction opposite to the first direction, the processor 110 may determine a second value which is the change amount of the intensity of the reflected light for a preset time.

According to various embodiments, the processor 110 may determine a blood flow direction based on the two change amount values. For example, the processor 110 may determine the blood flow direction based on the first value and the second value. For example, the change amount of the intensity of the reflected light measured when the movement direction of the light irradiated position is the same as the blood flow direction may be relatively smaller than the change amount of the intensity of the reflected light measured when the movement direction of the light irradiated position is opposite to the blood flow direction. For example, the change amount of the area of red blood cells in the cross-sectional area of the irradiated infrared light when the infrared light irradiated position is moved in the same direction as the blood flow direction may be relatively smaller than the change amount of the area of red blood cells in the cross-sectional area of the irradiated infrared light when the infrared light irradiated position is moved in the opposite direction to the blood flow direction. Therefore, the change amount of the intensity of reflected light measured when the infrared light irradiated position is moved in the same direction as the blood flow direction may be relatively smaller than the change amount of the intensity of the reflected light measured when the infrared light irradiated position is moved in the opposite direction to the blood flow direction.

According to various embodiments, the processor 110 may determine a smaller value of the first value and the second value, and may determine the movement direction of the light irradiated position at the time of measuring the smaller value to be the blood flow direction. For example, when the second value is smaller than the first value, the processor 110 may determine the direction B, which is the movement direction of the light irradiated position at the time of measuring the second value, to be the blood flow direction.

The blood flow measurement device 100 according to various embodiments may measure change amounts of the intensity of reflected light while moving the light irradiated position in two opposite directions, and may determine a blood flow direction by comparing the measured values.

According to various embodiments, the blood flow measurement device 100 may measure a change amount of the intensity of the reflected light for a preset time at a specific position, and may measure a change amount of the intensity of the reflected light for a preset time while moving a light irradiated position in a specific direction. For example, in response to non-movement of the light irradiated position, the processor 110 may determine a first value which is the change amount of the intensity of the reflected light for a preset time. For example, in response to the movement of the light irradiated position in a first direction, the processor 110 may determine a second value which is the change amount of the intensity of the reflected light for a preset time. According to various embodiments, the processor 110 may determine a blood flow direction based on the two change amount values.

Figure 4:
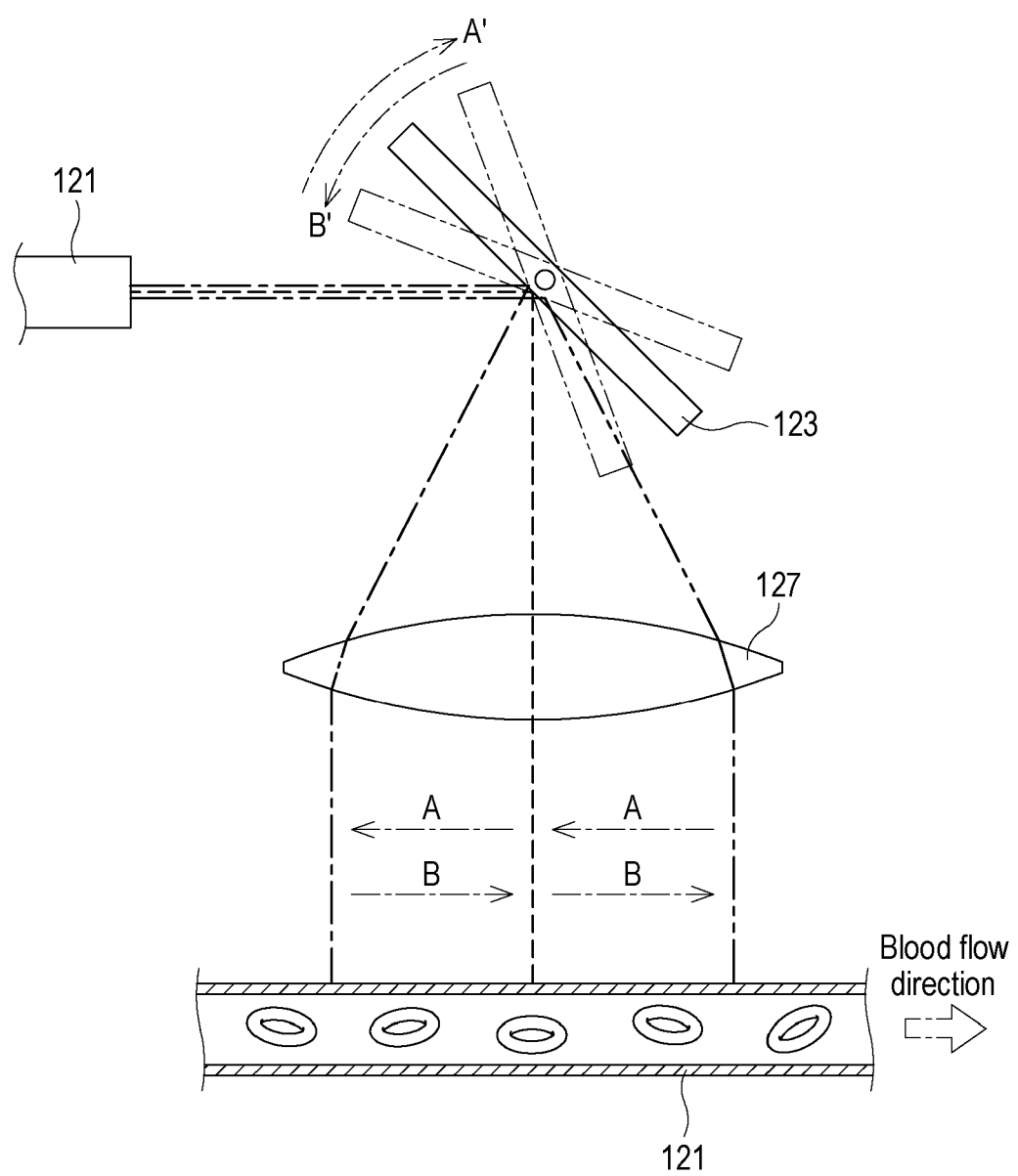
FIG. 4 illustrates a diagram of an operation of a blood flow measurement device according to various embodiments of the present disclosure.

FIG. 4 illustrates a diagram of an operation of the blood flow measurement device according to various embodiments of the present disclosure.

Referring to FIG. 4, according to various embodiments, the light outputted through the light source 121 may be reflected by the mirror 123 and may be incident on the lens 127. The light passing through the lens 127 may be irradiated to a specific position of a subject. According to various embodiments, the mirror 123 may be rotated about an arbitrary axis by a driving part (not shown) (e.g., the driving part 125 shown in FIG. 1).

The processor 110 according to various embodiments may control the light source 121 to radiate light while moving in a specific direction within a target region of the subject. The processor 110 may, for example, rotate the mirror 123 through the driving part 125 to move the irradiated position of the light outputted from the light source 121 in a specific direction.

For example, when trying to move the light irradiated position in an A direction, the processor 110 may rotate the mirror 123 in an A' direction by using the driving part 125. When the light source 121 outputs light while the mirror 123 is being rotated in the A' direction, the light irradiated position may be moved in the A direction.

For example, when trying to move the light irradiated position in a B direction, the processor 110 may rotate the mirror 123 in a B' direction by using the driving part 125. When the light source 121 outputs light while the mirror 123 is being rotated in the B' direction, the light irradiated position may be moved in the B direction.

For example, it may be assumed that the blood flow direction is substantially the same as the B direction. The change amount of the intensity of the reflected light measured while moving the light irradiated region in the B direction may be relatively smaller than the change amount of the intensity of the reflected light measured while moving the light irradiated region in the A direction. In this case, the processor 110 may determine the blood flow direction to be the B direction.

Figure 5A:
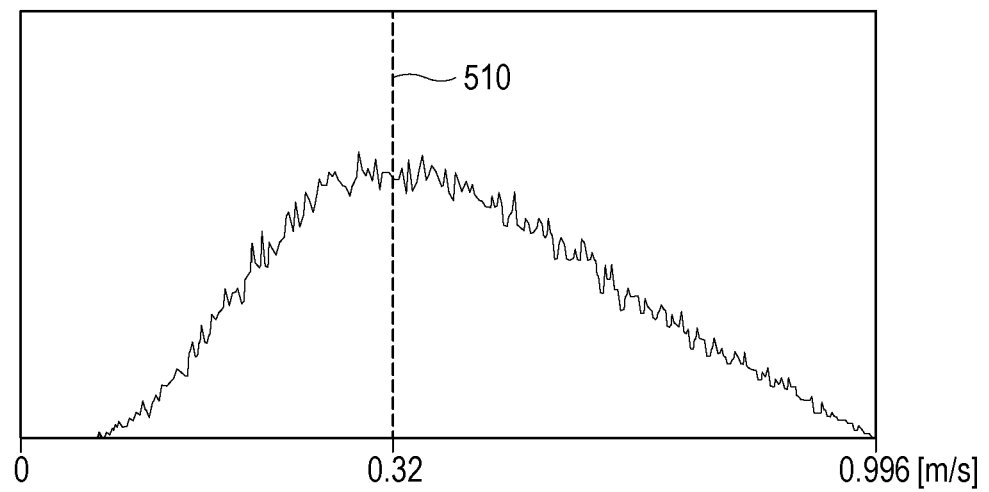
FIGS. 5A, 5B, and 5C illustrate diagrams of frequencies according to a value of a blood flow velocities calculated by measuring the change amount of the intensities of reflected light according to various embodiments of the present disclosure.
Figure 5B:
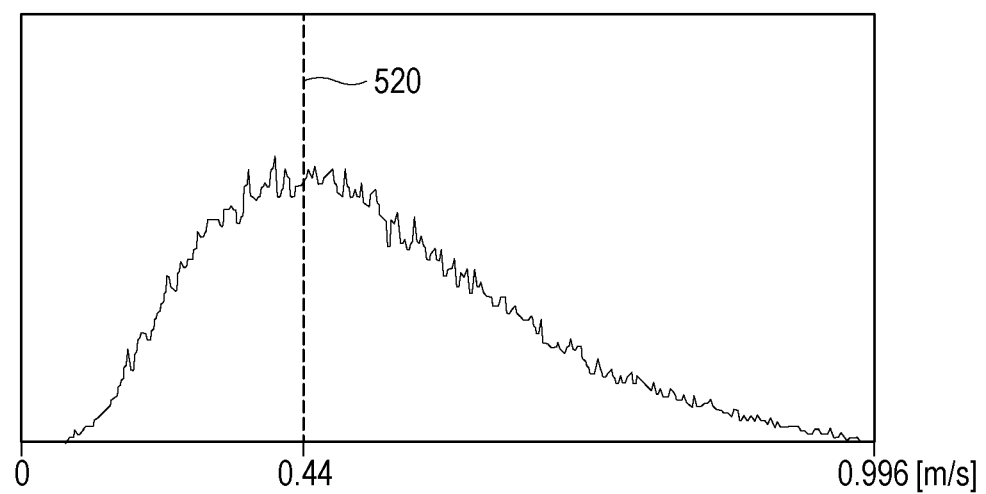
Figure 5C:
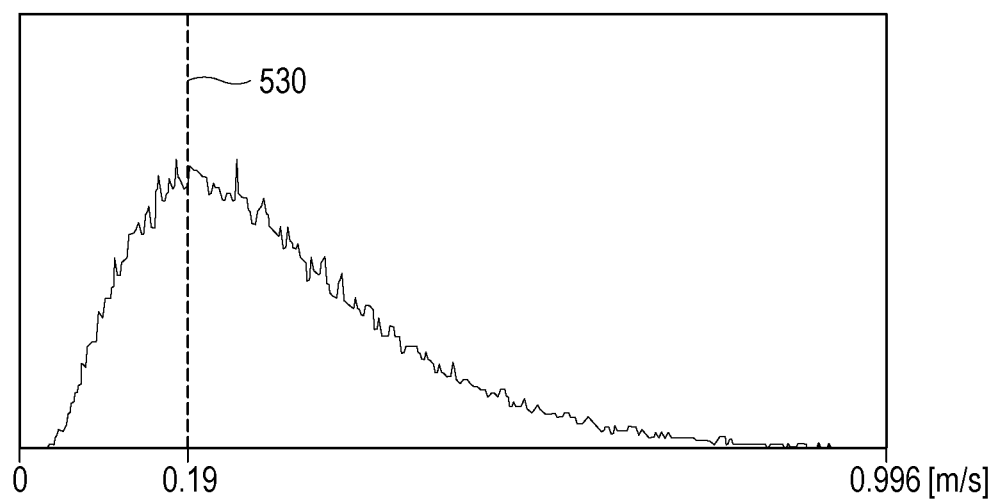

FIGS. 5A, 5B, and 5C illustrate diagrams of the frequencies according to the value of the blood flow velocities calculated by measuring the change amount of the intensities of reflected light according to various embodiments of the present disclosure. FIG. 5A is a graph showing the frequency according to the calculated blood flow velocity values obtained by calculating the blood flow velocity a plurality of times while irradiating light to a predetermined position. FIG. 5B is a graph showing the frequency according to the calculated blood flow velocity values obtained by calculating the blood flow velocity a plurality of times while moving the light irradiated position in the direction opposite to the blood flow direction. FIG. 5C is a graph showing the frequency according to the calculated blood flow velocity values obtained by calculating the blood flow velocity a plurality of times while moving the light irradiated position in the same direction as the blood flow direction. In FIGS. 5A, 5B, and 5C, the x-axis represents the blood flow velocity (m/sec) calculated based on the change amount of the intensities of the reflected light, and the y-axis represents the frequency.

In FIGS. 5A, 5B, and 5C, it is assumed that the blood flow velocity in the blood vessel having an actual blood flow velocity of 0.31 m/sec among the blood vessels of a subject is measured by the blood flow measurement device 100. The values described with reference to FIGS. 5A, 5B, and 5C are merely exemplary values to facilitate understanding.

Referring to FIG. 5A, the processor 110 according to various embodiments may measure the intensities of reflected light twice while irradiating light to a certain position of a subject, may determine a difference between the measured values as a change amount of the intensity of the reflected light, and may calculate a blood flow velocity corresponding to the determined change amount of the intensity of the reflected light based on the pre-stored conversion information. The graph of FIG. 5A may be obtained by repeating the operation of calculating the blood flow velocity a plurality of times. The processor 110 may determine, for example, the most frequently measured value 510 as a blood flow velocity. It can be seen that the blood flow velocity value measured while irradiating light to a certain position is determined to be 0.32 m/sec, which is similar to the actual blood flow velocity value of 0.31 m/sec.

Referring to FIG. 5B, the processor 110 according to various embodiments may measure the intensities of reflected light twice at a preset time interval while moving the light irradiated position in the opposite direction to the blood flow direction, may determine a difference between the measured values as a change amount of the intensity of the reflected light, and may calculate a blood flow velocity corresponding to the determined change amount of the intensity of the reflected light based on pre-stored conversion information. The graph of FIG. 5B may be obtained by repeating the operation of calculating the blood flow velocity a plurality of times. The processor 110 may determine, for example, the most frequently measured value 520 as the blood flow velocity. It can be seen that the blood flow velocity value measured while moving the light irradiated position in the opposite direction to the blood flow direction is determined to be 0.44 m/sec, which is larger than the actual blood flow velocity value of 0.31 m/sec.

Referring to FIG. 5C, the processor 110 according to various embodiments may measure the intensities of reflected light twice while moving the light irradiated position in the same direction as the blood flow direction, may determine a difference between the measured values as a change amount of the intensity of the reflected light, and may calculate a blood flow velocity corresponding to the determined change amount of the intensity of the reflected light based on pre-stored conversion information. The graph of FIG. 5C may be obtained by repeating the operation of calculating the blood flow velocity a plurality of times. The processor 110 may determine, for example, the most frequently measured value 530 as the blood flow velocity. It can be seen that the blood flow velocity value measured while moving the light irradiated position in the same direction as the blood flow direction is determined to be 0.19 m/sec, which is smaller than the actual blood flow velocity value of 0.31 m/sec.

Figure 6:
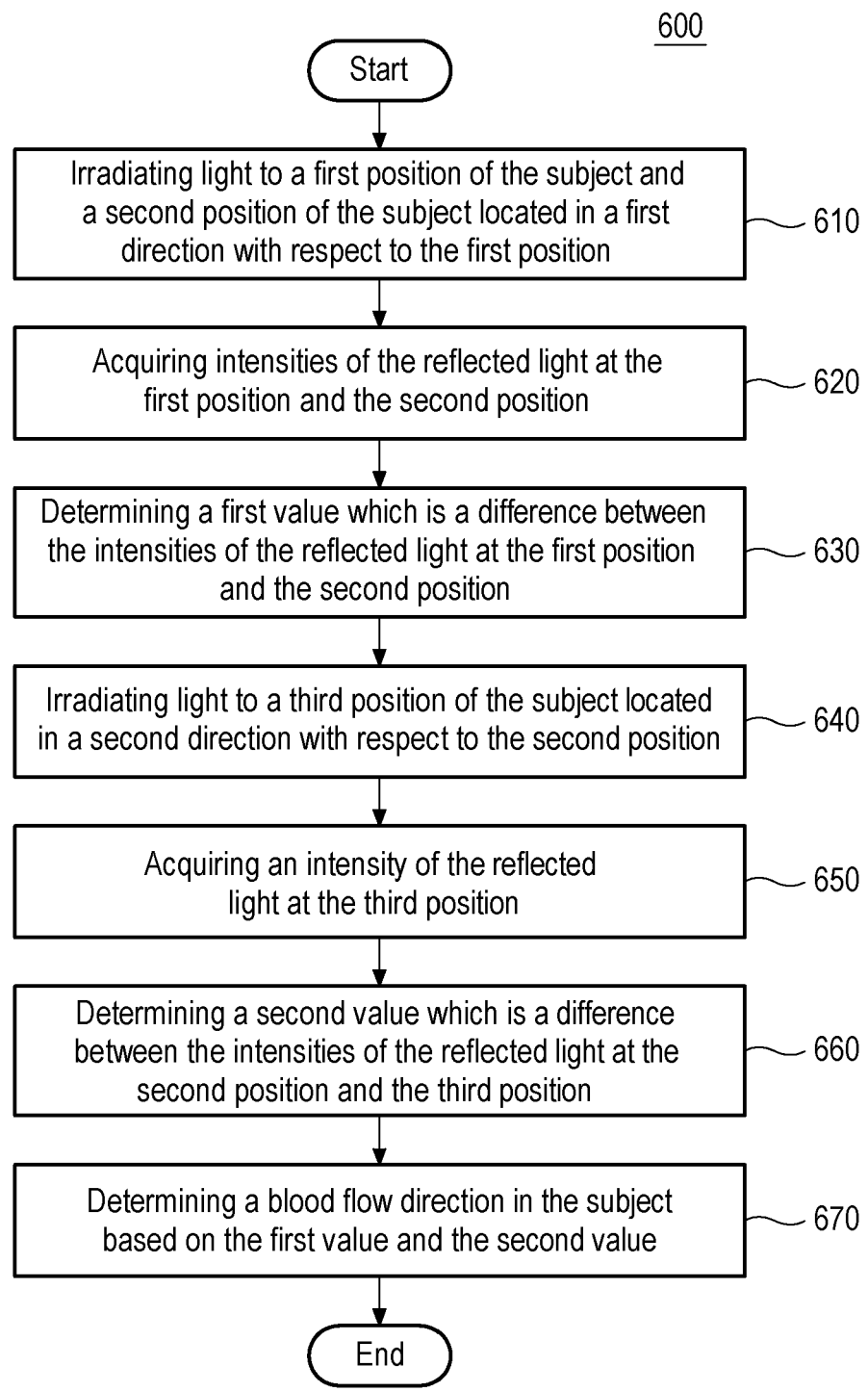
FIG. 6 illustrates an operational flow chart of a blood flow measurement device according to various embodiments of the present disclosure.

FIG. 6 illustrates an operational flow chart of the blood flow measurement device according to various embodiments of the present disclosure.

Referring to the operational flow chart 600, in operation 610, the processor 110 according to various embodiments may control the light output device 120 so as to irradiate light to a first position and a second position of a subject. The second position may be, for example, a position existing in the first direction from the first position. For example, the processor 110 may move the light irradiated position from the first position in the first direction by rotating the mirror 123 in the corresponding direction by using the driving part 125. For example, the processor 110 may irradiate light to the first position by using the light output device 120 and may irradiate light to the second position after a preset time has elapsed from irradiation of light to the first position.

In operation 620, the processor 110 according to various embodiments may acquire the intensities of the reflected light at the first position and the second position from the light receiving sensor 130 that receives the reflected light reflected at each of the first position and the second position. For example, when the light is irradiated to the second position of the subject, the light receiving sensor 130 may measure the intensity of reflected light and transmit it to the processor 110.

In operation 630, the processor 110 according to various embodiments may determine a first value, which is a difference between the intensities of the reflected light measured at the first position and the second position.

In operation 640, the processor 110 according to various embodiments may control the light output device 120 to irradiate light to a third position located in a second direction opposite to the first direction with respect to the second position. For example, the processor 110 may rotate the mirror 123 in the corresponding direction by using the driving part 125 while outputting light through the light source 121 of the light output device 120, thereby moving the light irradiated position in the second direction from the second position. For example, the processor 110 may irradiate light to the third position after a preset time has elapsed from the irradiation of light to the second position by using the light output device 120.

In operation 650, the processor 110 according to various embodiments may acquire the intensity of the reflected light at the third position from the light receiving sensor 130 that receives the reflected light reflected at the third position. For example, the light receiving sensor 130 may measure the intensity of reflected light when the light is irradiated to the second position of the subject, may measure the intensity of reflected light when the light is irradiated to the third position of the subject after a preset time has elapsed, and may transmit the measured intensities of the reflected light to the processor 110.

In operation 660, the processor 110 according to various embodiments may determine a second value, which is a difference between the intensities of the reflected light measured at the second position and the third position.

In operation 670, the processor 110 according to various embodiments may determine a blood flow direction in the subject based on the first value and the second value. For example, when the first value is smaller than the second value, the processor 110 may determine the blood flow direction in the subject as the first direction. For example, when the first value is larger than the second value, the processor 110 may determine the blood flow direction in the subject as the second direction.

Figure 7:
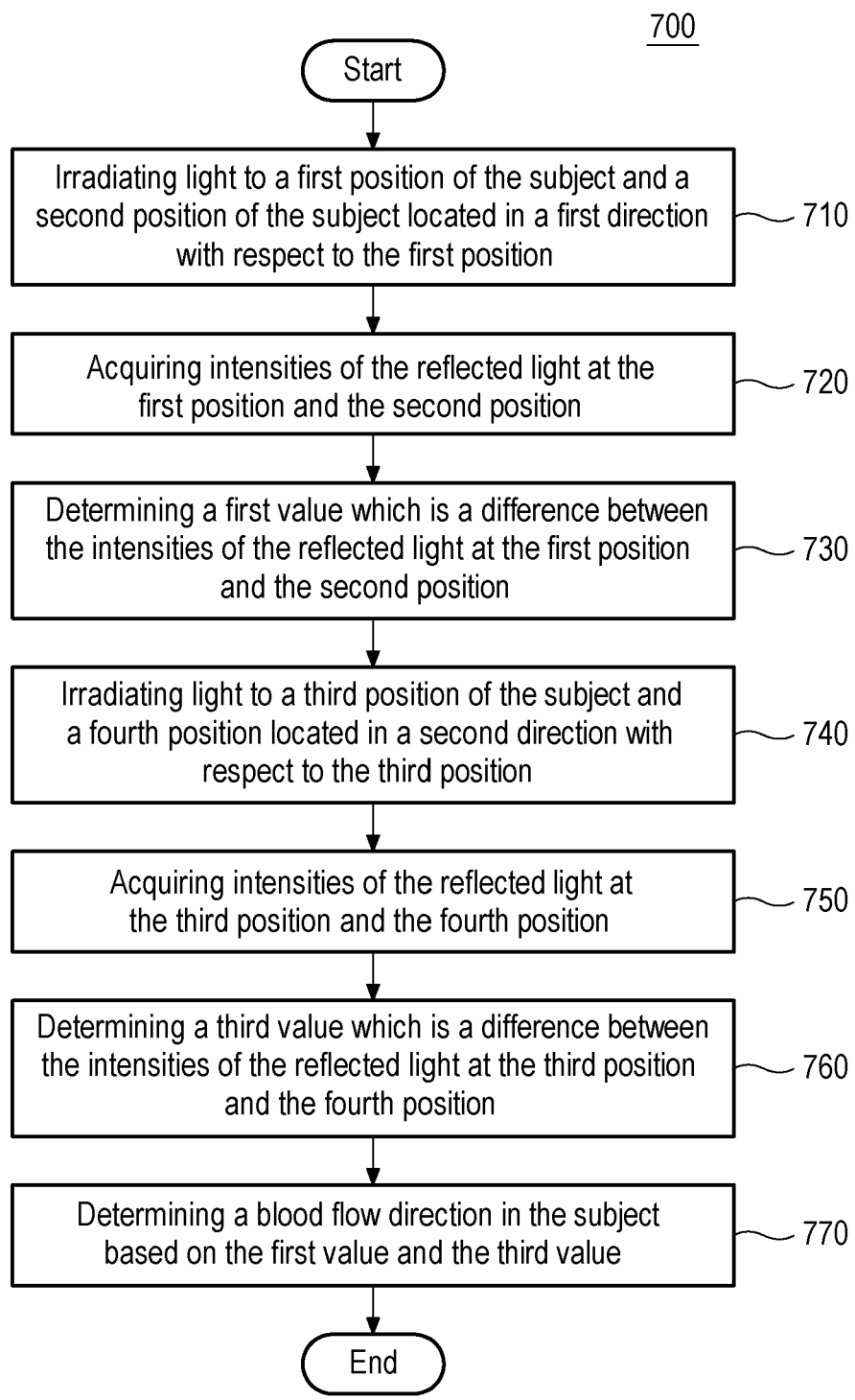
FIG. 7 illustrates an operational flow chart of a blood flow measurement device according to various embodiments of the present disclosure.

FIG. 7 illustrates an operational flow chart of the blood flow measurement device according to various embodiments of the present disclosure.

Referring to the operational flow chart 700, according to various embodiments, in operation 710, the processor 110 may control the light output device 120 to irradiate light to a first position and a second position of a subject. The second position may be, for example, a position existing in the first direction with respect to the first position. For example, the processor 110 may move the light irradiated position in the first direction from the first position by rotating the mirror 123 in the corresponding direction by using the driving part 125. For example, the processor 110 may irradiate light to the first position through the light output device 120 and may irradiate light to the second position after a preset time has elapsed from irradiation of light to the first position.

In operation 720, the processor 110 according to various embodiments may acquire the intensities of the reflected light at the first position and the second position from the light receiving sensor 130 that receives the reflected light reflected at the first position and the second position. For example, the light receiving sensor 130 may measure the intensity of the reflected light when the light is irradiated to the first position of the subject and may transmit the measured intensity of the reflected light to the processor 110. After a preset time has elapsed, the light receiving sensor 130 may measure the intensity of the reflected light when the light is irradiated to the second position of the subject and may transmit the measured intensity of the reflected light to the processor 110.

According to various embodiments, in operation 730, the processor 110 may determine a first value, which is a difference between the intensities of the reflected light measured at the first position and the second position.

According to various embodiments, in operation 740, the processor 110 may control the light output device 120 to irradiate light to a third position and a fourth position of the subject. The fourth position may be, for example, a position that exists in a second direction from the third position. The second direction may be, for example, a direction opposite to the first direction. For example, the processor 110 may rotate the mirror 123 in the corresponding direction by using the driving part 125 while outputting the light through the light source 121 of the light output device 120, thereby moving the light irradiated position in the second direction from the third position. For example, the processor 110 may irradiate the light to the third position by using the light output device 120 and may irradiate the light to the fourth position after a preset time has elapsed from irradiation of light to the third position.

In operation 750, the processor 110 according to various embodiments may acquire the intensities of the reflected light at the third position and the fourth position from the light receiving sensor 130 that receives the reflected light reflected at the third position and the fourth position. For example, the light receiving sensor 130 may measure the intensity of the reflected light when the light is irradiated to the third position of the subject and may transmit the measured intensity of the reflected light to the processor 110. After a preset time has elapsed, the light receiving sensor 130 may measure the intensity of the reflected light when the light is irradiated to the fourth position of the subject and may transmit the measured intensity of the reflected light to the processor 110.

In operation 760, the processor 110 according to various embodiments may determine a third value, which is a difference between the intensities of the reflected light measured at the third position and the fourth position.

In operation 770, the processor 110 according to various embodiments may determine a blood flow direction in the subject based on the first value and the third value. For example, when the first value is smaller than the third value, the processor 110 may determine the blood flow direction in the subject as the first direction. For example, when the first value is larger than the third value, the processor 110 may determine the blood flow direction in the subject as the second direction.

Figure 8:
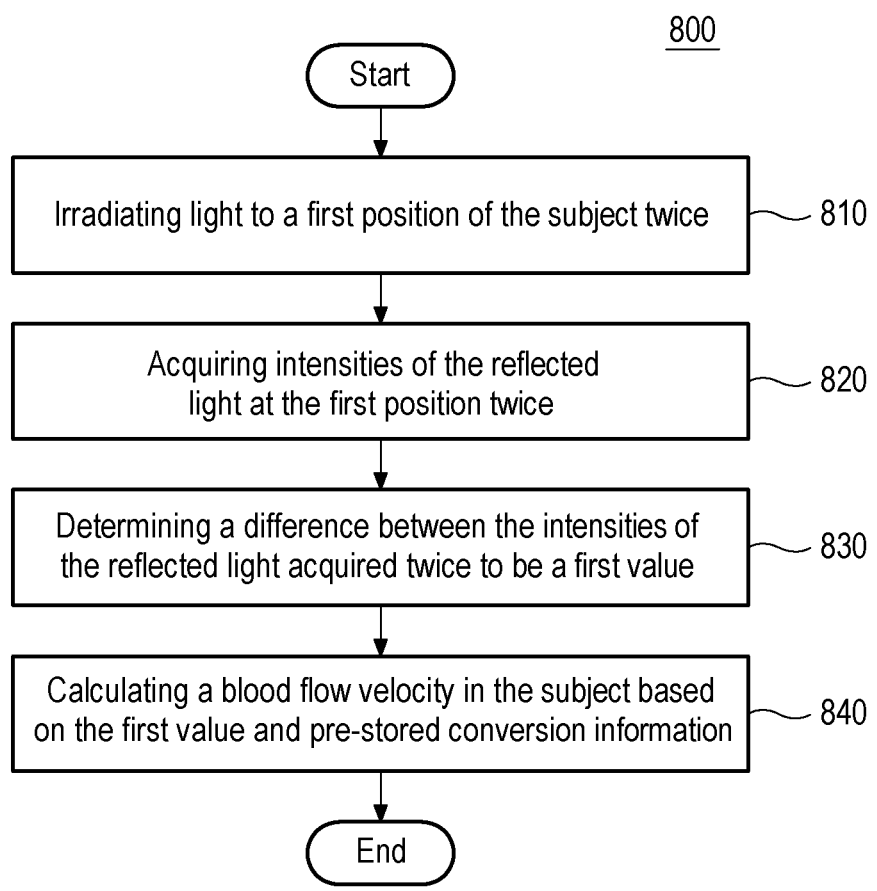
FIG. 8 illustrates an operational flow chart of a blood flow measurement device according to various embodiments of the present disclosure.

FIG. 8 illustrates an operational flow chart of the blood flow measurement device according to various embodiments of the present disclosure.

Referring to the operational flowchart 800, in operation 810, the processor 110 according to various embodiments may control the light output device 120 to irradiate light to a first position of a subject. The processor 110 according to various embodiments may control the light output device 120 to irradiate the light to the first position twice. For example, the processor 110 may control the light output device 120 to irradiate the light to the first position twice at a preset time interval.

In operation 820, the light receiving sensor 130 according to various embodiments may measure the intensities of the reflected light from the first position twice. For example, the light receiving sensor 130 may receive the reflected light from the first position twice at a preset time interval, may generate electrical signals indicating the intensities of the received light, and may transmit the signals to the processor 110. The processor 110 may acquire the intensities of the reflected light at the first position from the light receiving sensor 130 twice at a preset time interval.

In operation 830, the processor 110 according to various embodiments may determine a difference between the values obtained twice to be a first value.

In operation 840, the processor 110 according to various embodiments may calculate a blood flow velocity based on the determined difference value and the pre-stored conversion information. The pre-stored conversion information may include, for example, information on a correlation among an acquired difference value of reflected light intensities, a blood flow velocity, and a Doppler frequency.

Figure 9:
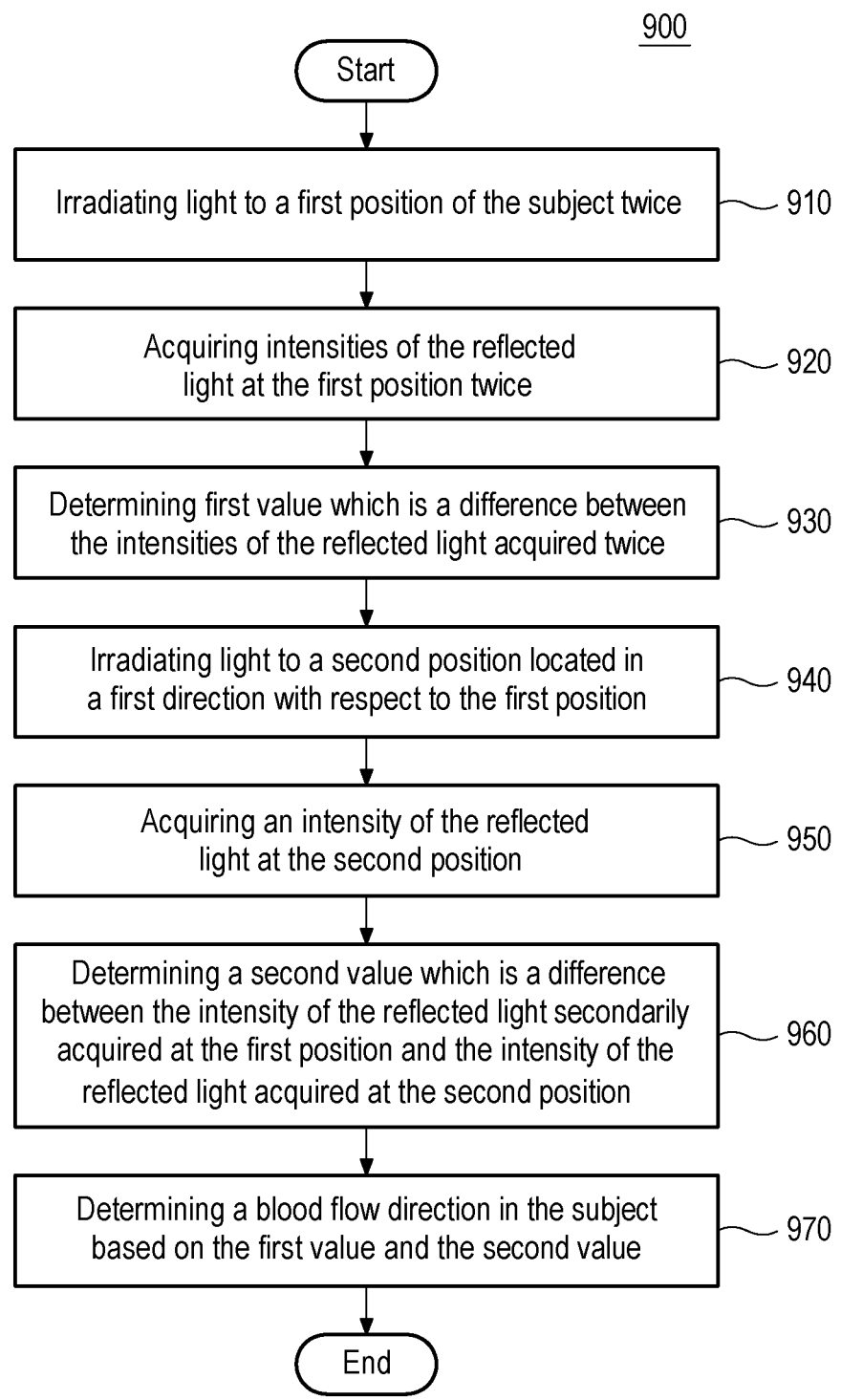
FIG. 9 illustrates an operational flow chart of a blood flow measurement device according to various embodiments of the present disclosure.

FIG. 9 is an operational flowchart of the blood flow measurement device according to various embodiments of the present disclosure.

Referring to the operational flowchart 900, in operation 910, the processor 110 according to various embodiments may control the light output device 120 to irradiate light to a first position of a subject twice. For example, the processor 110 may control the light output device 120 to irradiate light to the first position twice at a preset time interval.

In operation 920, the light receiving sensor 130 according to various embodiments may measure the intensities of the reflected light from the first position twice. For example, the light receiving sensor 130 may receive the reflected light from the first position twice at a preset time interval, may generate electrical signals indicating the intensities of the received light, and may transmit the electrical signals to the processor 110. The processor 110 may acquire the intensities of the reflected light at the first position from the light receiving sensor 130 twice at a preset time interval.

In operation 930, the processor 110 according to various embodiments may determine a difference between the values obtained twice to be a first value.

In operation 940, the processor 110 according to various embodiments may control the light output device 120 to irradiate light to a second position located in a first direction with respect to the first position. The processor 110 may irradiate the light to the first position twice by using the light output device 120 and may irradiate the light to the second position after a preset time has elapsed from irradiation of light to the first position. For example, the processor 110 may control the light output device 120 to irradiate light to the first position for a second time and to irradiate the light to the second position after a preset time has elapsed from irradiation of light to the first position for the second time.

In operation 950, the processor 110 according to various embodiments may acquire the intensity of the reflected light at the second position from the light receiving sensor 130 that receives the reflected light reflected at the second position.

In operation 960, the processor 110 according to various embodiments may determine a second value, which is a difference between the intensity of the reflected light secondarily acquired at the first position and the intensity of the reflected light acquired at the second position.

In operation 970, the processor 110 according to various embodiments may determine a blood flow direction in the subject based on the first value and the second value.

Figure 10:
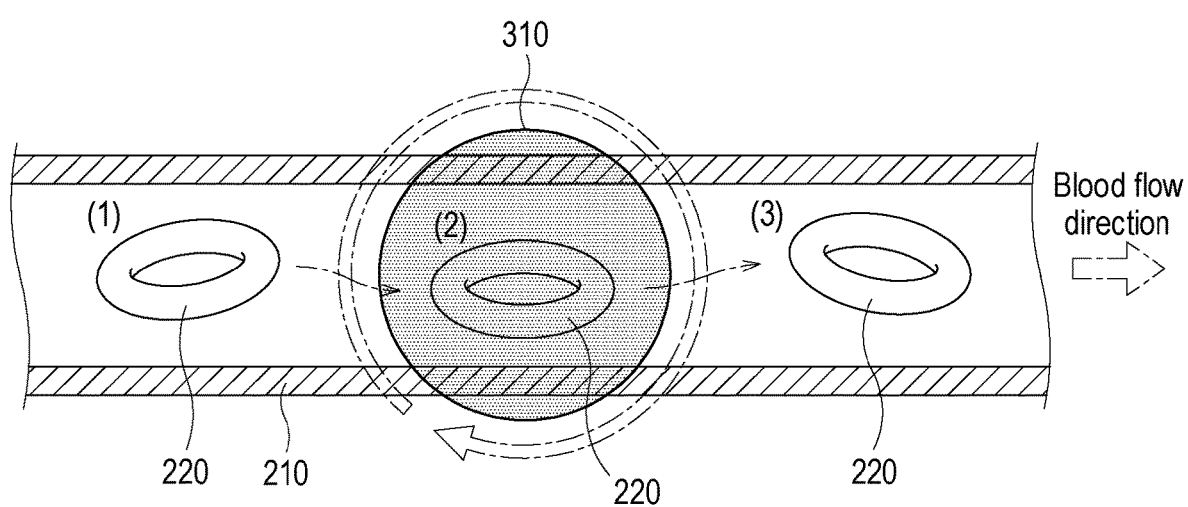
FIG. 10 illustrates a diagram of a blood flow measurement method according to various embodiments of the present disclosure.

FIG. 10 illustrates a diagram of a blood flow measurement method according to various embodiments of the present disclosure.

Referring to FIG. 10, the processor 110 according to various embodiments may circularly move a light irradiated position within a target region of a subject while irradiating light by using the light output device 120.

The processor 110 according to various embodiments may acquire the intensity of the reflected light by the subject from the light receiving sensor 130 while circularly moving the light irradiated position, and may determine the change amount of the intensities of the reflected light at least twice. For example, in response to the circular movement of the light irradiated position, the processor 110 may acquire the intensity of the reflected light at least four times at a preset time interval from the light receiving sensor 130. The processor 110 may determine the change amount of the intensities of the reflected light at least twice based on the intensities of the reflected light acquired at least four times.

The processor 110 according to various embodiments may determine a blood flow direction based on the change amounts of the intensities of the reflected light determined at least twice. For example, the processor 110 may determine the smallest value among the change amounts of the intensities of the reflected light determined at least twice. For example, the processor 110 may identify positions where the change amount having the smallest value is measured. For example, the processor 110 may determine a position vector based on the identified positions, and may determine a direction indicated by the determined position vector to be a blood flow direction.

What is claimed is:

1. A blood flow measurement device, comprising:
   a light output device configured to output light of a preset wavelength band;
   a light receiving sensor configured to receive the light outputted from the light output device and reflected by a subject; and
   a processor,
   wherein the processor is configured to:
   control the light output device to irradiate light to a first position of the subject and a second position of the subject located in a first direction with respect to the first position,
   acquire intensities of the reflected light at the first position and the second position from the light receiving sensor that receives the reflected light reflected at the first position and the second position,
   determine a first value which is a difference between the intensities of the reflected light at the first position and the second position,
   control the light output device to irradiate light to a third position of the subject located in a second direction opposite to the first direction with respect to the second position,
   acquire an intensity of the reflected light at the third position from the light receiving sensor that receives the reflected light reflected at the third position,
   determine a second value which is a difference between the intensities of the reflected light at the second position and the third position, and
   determine a blood flow direction in the subject based on the first value and the second value.

2. The blood flow measurement device of claim 1, wherein the processor is configured to determine the blood flow direction in the subject as the first direction when the first value is smaller than the second value.

3. The blood flow measurement device of claim 1, wherein the light output device comprises:
   a light source configured to output light of the preset wavelength band;
   a mirror configured to reflect the light outputted from the light source to change a path of the light; and
   a driving part configured to adjust an angle of the mirror,
   wherein the processor is configured to rotate the mirror using the driving part to irradiate light to the subject while moving in the first direction or the second direction.

4. The blood flow measurement device of claim 3, wherein the light output device further comprises a lens configured to collimate the light reflected from the mirror.

5. The blood flow measurement device of claim 1, wherein the processor is configured to:
   control the light output device to irradiate light to the first position and irradiate light to the second position after a preset time has elapsed from irradiation of the light to the first position, and
   control the light output device to irradiate light to the third position after the preset time has elapsed from irradiation of the light to the second position.

6. The blood flow measurement device of claim 1, wherein the processor is configured to:
   control the light output device to irradiate light to a fourth position located in the first direction with respect to the third position of the subject before controlling the light output device to irradiate light to the third position,
   acquire an intensity of the reflected light at the fourth position from the light receiving sensor that receives the reflected light reflected at the fourth position,
   determine a third value which is a difference between the intensities of the reflected light at the fourth position and the third position, and
   determine the blood flow direction in the subject based on the first value and the third value.

7. A blood flow measurement method using a blood flow measurement device comprising a light output device configured to output light of a preset wavelength band, a light receiving sensor configured to receive the light outputted from the light output device and reflected by a subject, and a processor, the method comprising:
- irradiating, by the light output device, light to a first position of the subject and a second position of the subject located in a first direction with respect to the first position;
- acquiring, by the processor, intensities of the reflected light at the first position and the second position from the light receiving sensor that receives the reflected light reflected at the first position and the second position;
- determining, by the processor, a first value which is a difference between the intensities of the reflected light at the first position and the second position;
- irradiating, by the light output device, light to a third position of the subject located in a second direction opposite to the first direction with respect to the second position;
- acquiring, by the processor, an intensity of the reflected light at the third position from the light receiving sensor that receives the reflected light reflected at the third position;
- determining, by the processor, a second value which is a difference between the intensities of the reflected light at the second position and the third position; and
- determining, by the processor, a blood flow direction in the subject based on the first value and the second value.

8. The method of claim 7, wherein determining the blood flow direction comprises determining the blood flow direction in the subject as the first direction when the first value is smaller than the second value.

9. The method of claim 7, wherein irradiating, by the light output device, light to the first position of the subject and the second position of the subject comprises irradiating light to the first position and irradiating light to the second position after a preset time has elapsed from irradiation of light to the first position through the light output device, and
- irradiating, by the light output device, light to the third position of the subject comprises irradiating light to the third position after the preset time has elapsed from irradiation of the light to the second position through the light output device.

10. The method of claim 7, further comprising:
- irradiating, by the light output device, light to a fourth position located in the first direction with respect to the third position of the subject before the irradiating light to the third position;
- acquiring, by the processor, an intensity of the reflected light at the fourth position from the light receiving sensor;
- determining, by the processor, a third value which is a difference between the intensities of the reflected light at the fourth position and the third position; and
- determining, by the processor, the blood flow direction in the subject based on the first value and the third value.

* * * * *